(12) United States Patent
Schmitt et al.

(10) Patent No.: US 8,674,133 B2
(45) Date of Patent: Mar. 18, 2014

(54) METHOD FOR CONTINUOUSLY PRODUCING ALKYLAMINO(METH)ACRYLAMIDES

(75) Inventors: Bardo Schmitt, Mainz-Kastel (DE); Wolfgang Klesse, Mainz (DE); Martina Ebert, Dieburg (DE); Dirk Broell, Langen (DE); Guido Protzmann, Bensheim (DE); Joachim Knebel, Alsbach-Haehnlein (DE); Thomas Kehr, Muehltal (DE); Hans-Gerhard Stadler, Lorsch (DE); Gerhard Koelbl, Gernsheim (DE); Benedikt Laux, Monzernheim (DE)

(73) Assignee: Evonik Röhm GmbH, Darmstadt (DE)

( * ) Notice: Subject to any disclaimer, the term of this patent is extended or adjusted under 35 U.S.C. 154(b) by 244 days.

(21) Appl. No.: 13/254,280

(22) PCT Filed: Mar. 3, 2010

(86) PCT No.: PCT/EP2010/052689
§ 371 (c)(1),
(2), (4) Date: Sep. 1, 2011

(87) PCT Pub. No.: WO2010/115666
PCT Pub. Date: Oct. 14, 2010

(65) Prior Publication Data
US 2011/0313195 A1    Dec. 22, 2011

(30) Foreign Application Priority Data
Apr. 7, 2009 (DE) .......... 10 2009 002 239

(51) Int. Cl.
*C07C 231/02*    (2006.01)

(52) U.S. Cl.
USPC .............. 564/134; 564/135; 564/204

(58) Field of Classification Search
USPC .......... 564/134, 135, 204
See application file for complete search history.

(56) References Cited

U.S. PATENT DOCUMENTS

| 7,723,543 B2 * | 5/2010 | Schleep et al. ........ 564/134 |
| 2007/0149811 A1 | 6/2007 | Schleep et al. |
| 2009/0149674 A1 | 6/2009 | Schleep et al. |

FOREIGN PATENT DOCUMENTS

| CN | 101027276 A | 8/2007 |
| WO | 2004 103952 | 12/2004 |
| WO | 2006 056366 | 6/2006 |

OTHER PUBLICATIONS

International Search Report Issued Jun. 15, 2010 in PCT/EP10/052689 filed Mar. 3, 2010.
Chinese Office Action issued Jul. 17, 2013, in China Patent Application No. 201080014310.9 (with English translation).

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

The invention relates to a process for continuously preparing N-alkyl(meth)acrylamides by reacting alkyl(meth)acrylates with high-boiling amines. A catalyst activation and specific workup technique achieve product qualities which have not been achieved to date. In addition, very high space-time yields and overall yields can be achieved.

20 Claims, 1 Drawing Sheet

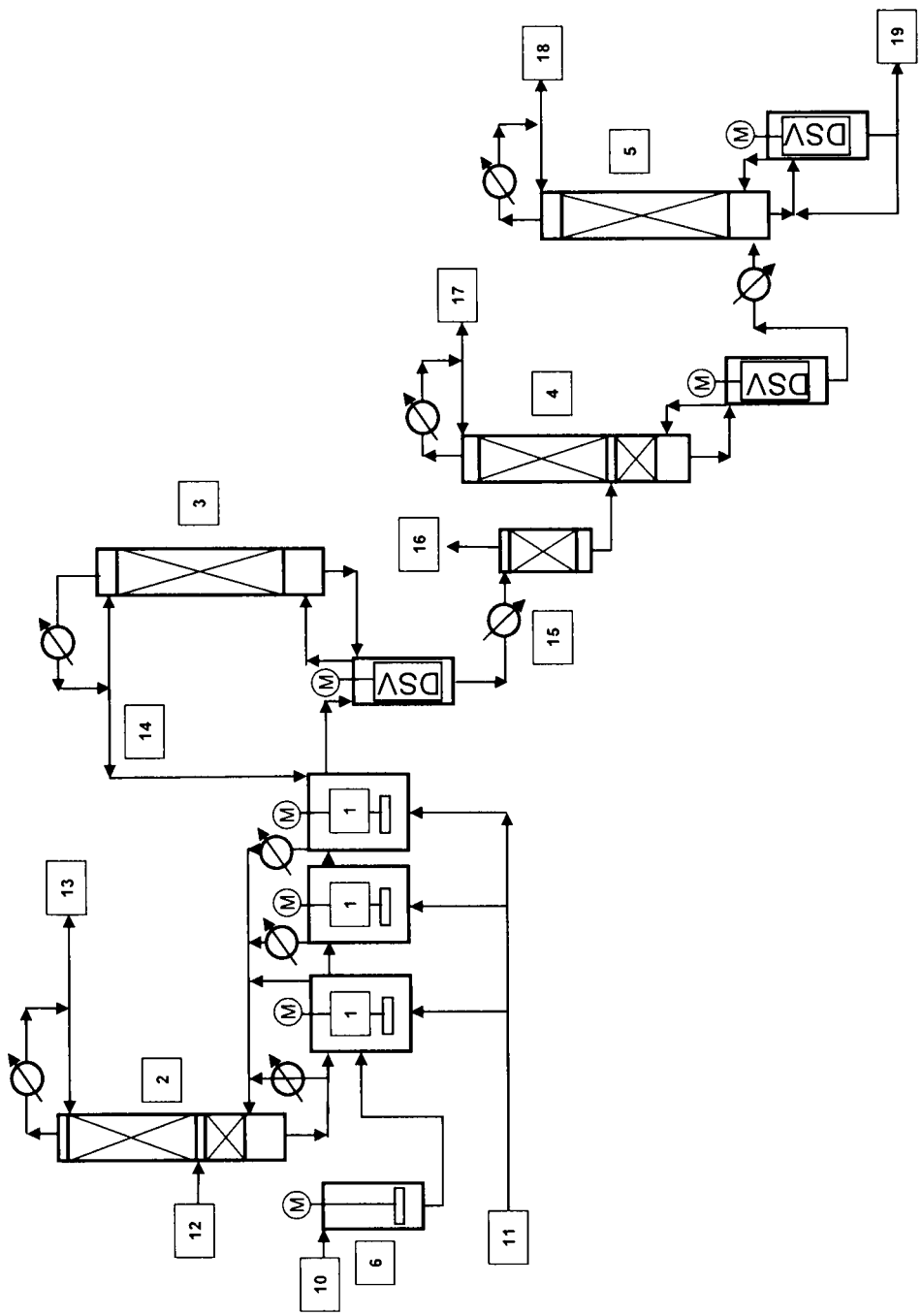

METHOD FOR CONTINUOUSLY PRODUCING ALKYLAMINO(METH)ACRYLAMIDES

This application is a 371 of PCT/EP2010/052689, filed Mar. 3, 2010.

FIELD OF THE INVENTION

The invention relates to a continuously operated process for preparing N-alkyl(meth)acrylamides (C) by continuous aminolysis of, for example, methyl(meth)acrylate (A where $R_1$=methyl) with amines (B) to release methanol (D where $R_1$=methyl) according to the following reaction equation:

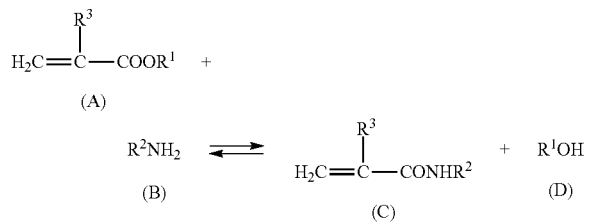

where:
$R^1$=linear or branched alkyl radical having 3 to 10 carbon atoms,
$R^3$ is hydrogen or the methyl group
$R^2$ is a linear, branched or cyclic alkyl radical, an aryl radical which may also be substituted by one or more alkyl groups, the linear, cyclic or branched alkyl radical may have a length of 1-12 carbon atoms, and may, for example, be methyl, ethyl, propyl, isopropyl, butyl, isobutyl, tert-butyl, pentyl, hexyl, heptyl, octyl, isooctyl, nonyl, decyl, undecyl, and may optionally be mono- or polysubstituted by
$NR^3R^4$ or
$OR^5$
where either $R^3$ or $R^4$ may assume the definition of hydrogen, and where, in addition:
$R^3$, $R^4$ or $R^5$ may be either the same or different and are each an alkyl group having 1-12 carbon atoms, for example methyl, ethyl, propyl, isopropyl, butyl, isobutyl, tert-butyl, pentyl, hexyl, heptyl, octyl, isooctyl, nonyl, decyl, undecyl or hydrogen,
$R^2$ may additionally also be

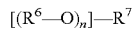

where:
$R^6$ may be a $C_1$-$C_4$-alkyl group which may also be branched, for example methyl, ethyl, propyl, isopropyl, butyl, isobutyl or tert-butyl,
$R^7$ may be the methyl group or the ethyl group.

Useful amines include, for example, the following compounds: dimethylaminoethylamine, diethylaminoethylamine, dipropylaminoethylamine, diisopropylaminoethylamine, dibutylaminoethylamine, diisobutylaminoethylamine, dimethylaminopropylamine, diethylaminopropylamine, dipropylaminopropylamine, diisopropylaminopropylamine, dibutylaminopropylamine, diisobutylaminopropylamine, dimethylaminobutylamine, diethylaminobutylamine, dipropylaminobutylamine, diisopropylaminobutylamine, dibutylaminobutylamine, diisobutylaminobutylamine, methylamine, cyclohexylamine, dimethylaminohexylamine, diethylaminohexylamine, dimethylaminoneopentylamine.

As well as dimethylaminopropylamine, particular preference is given to dimethylaminoethylamine, dimethylaminobutylamine, dimethylaminopentylamine and dimethylaminohexylamine.

STATE OF THE ART

The literature disclose many transesterification processes performed batchwise (batchwise transesterification processes) in conjunction with different catalysts.

The search for more economically viable processes led to the discovery of continuous transesterification processes in which the reactants are supplied continuously and the products are removed continuously. The continuous transesterification processes have the following advantages over the batchwise transesterification processes: the process is more easily automatable and can be conducted with a reduced personnel requirement, the product quality is better reproducible and less variable, the plant capacity is increased owing to the absence of the sequential execution of the individual preparation steps (filling, reaction, low boiler removal, product removal, emptying). The process possesses a higher space-time yield than a batchwise process.

Continuous transesterification processes are known.

EP 0 960 877 (Elf Atochem S. A.) describes a continuous process for preparing methacrylate esters of dialkylamino alcohols. Dialkylamino alcohols are reacted with generally methyl(meth)acrylate, and the dialkylaminoalkyl(meth)acrylate is obtained by the following process:

The mixture of the starting materials (methyl(meth)acrylate and dialkylamino alcohol) is fed together with a tetraalkyl titanate as a catalyst (for example tetrabutyl, tetraethyl or tetra(2-ethylhexyl) titanate) and at least one polymerization inhibitor (for example phenothiazine, tert-butylcatechol, hydroquinone monomethyl ether or hydroquinone) continuously to a stirred reactor, where the conversion to the dialkylaminoalkyl(meth)acrylate is effected at a temperature of 90° C.-120° C. with simultaneous continuous removal of the azeotropic methyl(meth)acrylate/methanol mixture. The crude reaction mixture (crude ester) is fed to a first distillation column, wherein an essentially catalyst-free stream is drawn off under reduced pressure at the top of the distillation column, and the catalyst and a little dialkylaminoalkyl(meth)acrylate are drawn off in the bottom of the distillation column. The top stream of the first distillation column is then fed to a second distillation column, in which a stream of low-boiling products with a low level of dialkylaminoalkyl(meth)acrylate is drawn off at the top under reduced pressure, and, in the bottom, a stream consisting of primarily dialkylaminoalkyl(meth)acrylate and polymerization inhibitor(s), which is fed to a third distillation column. In the third distillation column, a rectification is performed under reduced pressure, in which the desired pure dialkylaminoalkyl(meth)acrylate is drawn off at the top, and essentially the polymerization inhibitor or the polymerization inhibitors in the bottom. The bottom stream of the first distillation column is, after further purification with the aid of a film evaporator, recycled into the reactor just like the top stream from the second distillation column.

This process dispenses with dewatering of the alcohols before use, which can lead to increased deactivation of the tetraalkyl titanate used owing to hydrolysis up to and including the formation of undesired solid precipitates. Moreover, the process has the disadvantage that the catalyst is thermally stressed at relatively high temperatures in the bottom of the first distillation column. This can easily lead to the decomposition of the catalyst.

In this process, both the unconverted reactants and the product are rectified twice via the top in total. This entails very high energy costs and a total of 4 rectification columns, some of which have to have very large dimensions. The process is therefore afflicted with very high capital and operating costs.

EP 0 968 995 (Mitsubishi Gas Chemical Comp.) describes a continuous process for preparing alkyl(meth)acrylates using a reaction column. The transesterification reaction is effected directly in a distillation column (i.e. reactor and distillation column for removal of the methyl(meth)acrylate/methanol azeotrope form one apparatus), to which the starting materials (methyl(meth)acrylate and alcohol) are fed continuously. The catalyst needed, here likewise preferably a titanium compound, is present in the distillation column. In the case of a homogeneous catalyst, the catalyst is metered continuously into the distillation column. The use of homogeneous catalysts in a distillation column leads, however, owing to a purge effect by the liquid return stream in the distillation column, to an increased requirement for catalysts, and, in the case of occurrence of a solid catalyst precipitate, to soiling of the column internals. In the case of a heterogeneous catalyst, the catalyst is present in the reaction column. However, the positioning of the catalyst in the distillation column is disadvantageous because an increased pressure drop then occurs in the distillation column and, in addition, a very high level of cost and inconvenience is associated with the regular cleaning of the distillation column. In addition, heterogeneous catalysts can become deactivated, for example, owing to undesired polymerization.

DE 4 027 843 (Röhm GmbH) describes a continuous process for preparing N-substituted (meth)acrylamides by aminolysis of alkyl esters of (meth)acrylic acid with aliphatic and aromatic amines. The reaction temperature is >150° C., the pressure approx. 160 bar. No catalyst is employed.

CN 183 71 88 (Jiangsu Feixiang Chemical Co.) describes a process for preparing N-((3-dimethylamino)propyl)methacrylamide (DMAPMA) by reacting methyl methacrylate with N,N-dimethyl-1,3-propanediamine to give N-(3(-3-dimethylamino)propyl)-3-((dimethylamino)propyl)amino)-2-methylpropanamide (BDMAPA). BDMAPA is pyrolysed over the metal catalyst in a second reaction step at 160° C., and gives a DMAPMA with a purity of >97% in a 70% by weight yield. The process is described as a batchwise process. The content of crosslinkers is quite high.

WO 2004/103952 (Röhm GmbH) describes a process for continuously preparing alkylaminoacrylamides by reacting alkyl acrylates with high-boiling amines. A particular workup technique achieves product qualities which have not been attained to date. Moreover, very high space-time and overall yields can be achieved.

Problem

It is an object of the present invention to provide a continuous process of aminolysing (meth)acrylic esters, which avoids the disadvantages of the two processes described above. Moreover, the novel process shall provide a product with better quality than those present on the market to date. A better quality is understood to mean a lower crosslinker content or a lower content of addition products of the amines onto the double bond of the starting ester or onto the double bond of the product amide.

Qualities of the N-alkyl(meth)acrylamides available on the market to date have, for example, the following composition:

N-3-Dimethylaminopropylmethacrylamide (Jiangsu Feixiang Chemical Co., obtained in May 2008, Batch Number 2007/05/01) has a purity of 98.4% and a crosslinker content of 1.730 ppm. The crosslinker found was N-allylmethacrylamide.

It was thus an object of the invention to develop a process which leads to an N-alkyl(meth)acrylamide with a significantly lower crosslinker content.

In addition, the novel process shall provide amino(meth)acrylates with a minimum level of complexity and in a more energetically favourable (i.e. less expensive) manner. The personnel required to operate the plant shall be reduced.

Solution

These objects and further objects which are not detailed individually but which are directly discernible or derivable from the introductory discussion of the prior art are achieved by a process having the features of the present invention. Advantageous modifications of the process according to the invention are protected in the claims recited herein.

BRIEF DESCRIPTION OF THE DRAWING

The FIGURE shows a schematic diagram of a process flow according to an embodiment of the invention.

PROCESS DESCRIPTION

The process is shown schematically in FIG. 1.

EXPLANATIONS OF THE REFERENCE NUMBERS, FIG. 1

1. Reaction apparatus
2. Low boiler discharge distillation column
3. Low boiler distillation column
4. Crude column
5. Pure column
6. Catalyst preactivation
10. Catalyst feed
11. (Meth)acrylate feed
12. Amine feed
13. Low boiler discharge
14. Low boiler circulation stream
15. Crude product
16. Low boiler discharge
17. Lower boiler discharge
18. Pure product
19. High boiler discharge
DSV=Thin-film evaporator The (meth)acrylate feed, reactant (11), is fed continuously to a suitable reaction apparatus (1), wherein either an individual reaction vessel or a cascade of two or more reaction vessels connected in series can be used. Such a cascade may consist, for example, of 2, 3, 4, 5 or 6 or possibly more individual reaction vessels. In a preferred embodiment, a cascade of 3 continuous stirred tanks connected in series is used.

The (meth)acrylate feed, reactant (11), can be fed in in various ways. It is possible, for example, to feed the reactant stream (11) only to the first reaction vessel of the cascade, or else to divide the reactant stream (11) into substreams and to feed these substreams to all or only some of the reaction vessels connected in series in the cascade. It is equally possible to undertake the feeding of the reactant stream (11) via the apparatus (2) and/or the reaction apparatuses (1). It may be advantageous to feed the reactant stream (11) only into the apparatus (2) or, in a further embodiment, to divide the reactant stream (11) into substreams which are then supplied either to the apparatus (2) or to the first reaction vessel or if appropriate to two or more reaction vessels of the cascade.

It is advisable that all reaction vessels possess a vapour draw to the distillation column (2) for removal of the alcohol released in the reaction.

The flow regime into and out of the reactors need not necessarily be as shown in the flow diagram. In particular embodiments, it has been found to be advantageous to introduce the discharge from one tank of the cascade into the bottom of the next tank of the cascade downstream in each case.

The amine (12) is fed continuously to the distillation column (2) for dewatering.

The tetraalkoxy titanate required as the catalyst (the tetraalkoxy titanate content in relation to the (meth)acrylic ester A used is preferably 0.2% by weight-4% by weight) is, like the polymerization inhibitor(s) likewise preferably metered continuously into the reaction apparatus (1).

The aminolysis catalysts used may, however, also be all transesterification catalysts known from the prior art. Useful catalysts include, for example, zirconium acetylacetonate and further 1,3-diketonates of zirconium; it is also possible to use mixtures of alkali metal cyanates or alkali metal thiocyanates and alkali metal halides, and also tin compounds, for example dioctyltin oxide, alkaline earth metal oxides or alkaline earth metal hydroxides, for example CaO, Ca(OH)$_2$, MgO, Mg(OH)$_2$ or mixtures of the aforementioned compounds, and also alkali metal hydroxides, alkali metal alkoxides and lithium chloride and lithium hydroxide; it is also possible to use mixtures of the aforementioned compounds with the aforementioned alkaline earth metal compounds and the lithium salts, dialkyltin oxides, for example dioctyltin oxide, alkali metal carbonates, alkali metal carbonates together with quaternary ammonium salts, for example tetrabutylammonium hydroxide or hexadecyltrimethylammonium bromide, and also mixed catalysts composed of diorganyltin oxide and organyltin halide, acidic ionic exchangers, phosphorus-molybdenum heteropolyacids, titanium alkoxides, for example isopropyl titanate, chelate compounds of the metals titanium, zirconium, iron or zinc with 1,3-dicarbonyl compounds, lead compounds, for example lead oxides, lead hydroxides, lead alkoxides, lead carbonates or lead salts of carboxylic acids. Particular preference is given to a catalyst mixture of dialkyltin oxide and alkyl titanate, for example dioctyltin oxide and isopropyl titanate in a ratio of approx. 2.5:1 (% by weight/% by weight).

The catalyst or the catalyst mixture is used in amounts of 0.1% by weight-10% by weight, preferably 0.2% by weight-7% by weight, based in each case on the (meth)acrylate used.

Preactivation of the catalyst has been found to be advantageous (6). This involves mixing or dispersing the catalysts, heating them to temperatures of 90° C. to 120° C. and stirring for 2 to 3 h until a homogeneous, clear solution has formed.

Suitable alkyl(meth)acrylates are all (meth)acrylates having a linear or branched alkyl radical having 3 to 10, preferably 3 to 6 and more preferably 3 or 4 carbon atoms. Typical examples thereof are propyl(meth)acrylate, isopropyl(meth)acrylate, n-butyl(meth)acrylate, isobutyl(meth)acrylate, 3-methylbutyl(meth)acrylate, amyl(meth)acrylate, neopentyl(meth)acrylate, hexyl(meth)acrylate, cyclohexyl(meth)acrylate, heptyl(meth)acrylate, n-octyl(meth)acrylate, ethylhexyl(meth)acrylate or decyl(meth)acrylate.

The amines used may be all compounds $R^2NH_2$ whose $R^2$ radical consists of 1-12, preferably 2-8 or more preferably of 2-4 carbon atoms. Examples of typical structures and specific compounds have already been listed at the start of this application.

It is additionally clear to the person skilled in the art in the field that the starting materials are particularly advantageously selected such that the removal of the alcohol from the reaction mixture can shift the equilibrium to the side of the products. The alcohol can be removed distillatively by virtue of its lower boiling point compared to the amine used and/or by virtue of the formation of an azeotrope.

Useful polymerization inhibitors include hydroquinone, 4-hydroxy-2,2,6,6-tetramethylpiperidinooxyl or else bis(2-methoxycarbonylpropyl) sulfide or hydroquinone monomethyl ether in conjunction with oxygen.

The amine used may contain water. The amount of water in the amine used is between 50 and 500 ppm (0.05-0.005% by weight). Before entering the reaction apparatus, the amine is preferably dewatered distillatively by means of the distillation column (2). In the course of this, the water present in the amine is drawn off via the top. To prevent contamination of the lower boiler discharge (13) with the amine used, the amine is preferably added in the lower part of the distillation column (2). The amine used may also be dewatered in another way:

by means of an upstream dewatering distillation column or by means of treatment with a dewatering agent, for example a molecular sieve, or by means of a membrane separation process, for example a pervaporation.

The dewatering is important since the water present in the amine can lead to irreversible damage to the catalyst (e.g. tetraalkyl titanate) in the reactor. The water present in the amine leads to the formation of by-products and should therefore be strictly avoided. This dewatering step prevents the hydrolysis of the catalyst and the associated costs resulting from increased amounts of catalyst used and resulting from problems with solid precipitates. In addition, the purity of the product is increased by a reduced proportion of by-products.

The reaction is effected in the reaction apparatus (1) at a temperature in the range between 80° C. and 180° C. according to the system and operating pressure. The temperature range is preferably between 110° C. and 160° C. To increase the reaction rate, the alcohol released in the reaction is drawn off (13) from the reaction mixture by means of the distillation column (2), optionally also as an azeotrope with the alcohol. This can be done at atmospheric pressure, at elevated pressure or at reduced pressure. The reaction mixture, which consists for the most part of the product alkyl(meth)acrylamide, unconverted (meth)acrylate and amine, and also small amounts of alcohol, the catalyst, the polymerization inhibitors and a proportion of by-products, is fed after approx. 0.5-3 hours of reactor residence time (preference being given to a residence time of 1-2 hours) to a continuously operated falling-film evaporator (5). The vapours of the falling-film evaporator (5) are fed to a low boiler distillation column (3). In that column, the low-boiling components in relation to the product amide, predominantly product alcohol and unconverted reactant (meth)acrylate and amine, are removed under reduced pressure, preferably in the range of approx. 1 mbar-500 mbar. These are drawn off via the top of the distillation column (3) and recycled (14) into the reactor region or into the distillation column (2). This circulation stream achieves a high conversion based on the reactants and the overall process.

The crude amide (15) obtained in the outlet of the falling-film evaporator (5), which is still contaminated with catalyst, polymerization inhibitor and high-boiling by-products, contains preferably >80% by weight of product amide and is sent to the workup of a further vacuum distillation stage which works in the preferred pressure range between 0.1 and 200 mbar. The pure product amide is removed distillatively here as the top product.

The by-products formed in the process are high-boiling components in relation to the reactant amine and the reactant (meth)acrylate, and thus get into the product amide as an impurity, which significantly lowers the product quality. This problem can be solved by removing the product amide from the catalyst and the polymerization inhibitors and the high-boiling by-products using an apparatus with gentle film evaporation such as (5). Suitable apparatus for this purpose are falling-film, thin-film and short-path evaporators.

The preparation of the N-alkyl(meth)acrylamides may optionally be followed by a purifying distillation plant, which can also be operated under reduced pressure, for example at 500-0.1 mbar. This is required especially when a particularly good removal of the high-boiling secondary components formed in the process is to be effected. In the process according to the invention, a two-stage workup is used in order to achieve a low crosslinker content. In the first distillation, the crude product (15) is heated and metered to a column in the top in order to remove low boilers (16). The degassed feed stream is applied to the middle of a second column (4) in order to remove lower boilers (17). The lower boiler-free intermediate is applied to a third column (5), and the product (18) is distilled via the top in order to remove the high boilers in the bottoms (19) obtained.

The process according to the invention is illustrated in detail by the example which follows, without being restricted thereto.

EXAMPLE

Continuous Aminolysis to N-alkyl(meth)acrylamide

For continuous preparation of N-dimethylaminopropyl-methacrylamide, 200 kg/h of preactivated catalyst feed with a proportion of 2.0% by weight of isopropyl titanate were metered into the 1$^{st}$ reaction tank, 5.0% by weight of dioctyl-tin oxide to the distillation column (2), and 144 kg/h of N-dimethylaminopropyl-amine (DMAPA). The preactivation was performed at 110° C. in a stirred tank for 2 h. In addition, the circulation return stream from the top of the low boiler distillation column flowed continuously to the 1st reaction tank via the distillation column (2) (400 kg/h with the composition of 70% by weight of reactant methacrylate, and also methanol, DMAPA and by-products). The molar MMA:DMAPA ratio in the reactor feed was 1.8:1. In addition, the vapours from the stirred tank which had been freed of methanol in the distillation column (2) were fed to the 1st reaction tank via the column bottom. Under these reaction conditions (pressure approx. 500 mbar), a reaction temperature of 138° C. was established in the 1st reaction tank. The reaction temperatures in the 2nd and 3rd reaction tanks were 143 and 155° C. respectively. The distillate draw rate from the distillation column (2) was 110 kg/h.

The output from the 1st reaction tank was passed into the 2nd reaction tank, and the output from the 2nd reaction tank was passed into the 3rd reaction tank. With a total residence time of approx. 150 min, the following proportions of the components were determined at the outlet of the 3rd reaction tank:

| | |
|---|---|
| MMA | 43% by weight |
| DMAPA | 4.86% by weight |
| Amino amide | 35% by weight |

The vapours from the individual stirred tanks were fed continuously to the distillation column (2).

The output from the 3rd reaction tank was passed continuously to the thin-film evaporator of a low boiler column, in which unconverted DMAPA, MMA and methanol were drawn off as the distillate (400 kg/h) and fed back to the distillation column (2) as the circulation return stream. The bottoms discharge of the thin-film evaporator of the low boiler column was 240 kg/h and had the composition: approx 90% by weight of product amide, 0.1% by weight of DMAPA, a greater proportion of high-boiling components and traces of the reactants.

The crude product is subsequently worked up in a two-stage distillation.

First Distillation:

The crude product prepared (approx. 90% by weight of product amide) is conveyed batchwise into the reservoir vessel via a pipeline. Stabilizers are added there.

By means of a pump, the product, heated by a heater, is passed to the top of the column. The low boilers (16) removed are condensed if possible and sent to a thermal utilization. Uncondensable components are absorbed in sulfuric acid in the gas scrubbing plant.

The degassed feed stream is applied to the middle of the second column and freed there of lower boilers (17) by means of an evaporator. The lower boilers obtained are condensed and likewise utilized thermally.

Main Distillation:

The "lower boiler-free product" is collected and introduced into the third column via a preheater. The pure product (18) is drawn off via the top, almost completely condensed in the dephlegmator and transferred into the pure product tank.

Uncondensed components are liquefied in the downstream condenser and utilized thermally.

The high boilers are drawn off in the bottom of the second evaporator and sent to a thermal utilization (19).

The process according to the invention leads to a product (N-3-dimethylamino-propylmethacrylamide) with a purity of >98%, in the example 98.9%, and a content of less than 600 ppm, especially 500 ppm, more preferably less than 400 ppm, in the example 240 ppm, of crosslinker. The crosslinker found was N-allylmethacrylamide (analysis by GC).

Polymerization Experiment

Recipe: Solution polymer of N-3-dimethylamino-propyl-methacrylamide, 15% by weight in n-butyl acetate Conditions: 0.30% by weight of 2,2'-azobis(isobutyronitrile), based on monomer, 18 h at 70° C. in a water bath Inventive product: already contains 240 ppm by weight of N-allyl-methacrylamide (crosslinker);

Comparative 1 to 4: the inventive product is adjusted to the corresponding crosslinker content by adding N-allyl-methacrylamide

| | Crosslinker in the product | Visual assessment |
|---|---|---|
| Inventive product | 240 ppm | liquid |
| Comparative 1 | 600 ppm | gelated at the base |
| Comparative 2 | 1000 ppm | gelated |

| | Crosslinker in the product | Visual assessment |
|---|---|---|
| Comparative 3 | 1600 ppm | gelated |
| Comparative 4 | 2000 ppm | gelated |
| FEIXIANG | 1730 ppm | gelated |

The comparative experiments were intended to find out what amount of N-allylmethacrylamide crosslinker in the monomer exhibits significant effects in the application (polymerization).

The comparison with the commercially available product shows clearly that the crosslinker content in the product obtainable by the process according to the invention is significantly lower.

Even at 600 ppm of crosslinker, incipient gel formation is observed in the polymerization; at 1000 ppm, the mixture gelates completely.

The invention claimed is:

1. A process for preparation of a N-alkyl(meth)acrylamide, the method comprising:
   I) preactivating a catalyst by heating to a temperature of 90 to 120° C. to obtain a homogeneous catalyst solution;
   II) charging the preactivated catalyst to a reactor of a continuous reactor apparatus comprising the reactor, and a distillation column;
   III) continuously reacting an amine of formula (B) with an alkyl(methacrylate) of formula (A) in the reactor:

$$R^2NH_2 \quad (B)$$

wherein $R^2$ is a linear or branched or cyclic alkyl radical or aryl radical having 1 to 12 carbon atoms,

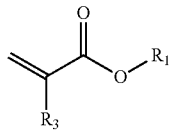
   (A)

wherein
   $R^1$ is a linear or branched alkyl radical having 3 to 10 carbon atoms, and
   $R^3$ is hydrogen or the methyl group,
   in the presence of the thermally preactivated catalyst or of a catalyst mixture and in the presence of at least one polymerization inhibitor;
   removing an alcohol or an alcohol/alkyl(meth)acrylate mixture from the reactor to the distillation column;
   conducting the reaction mixture from which the alcohol mixture is removed out of the reaction apparatus into a first distillation column or an evaporator connected to a first distillation column, wherein, by distillation under reduced pressure via a top of the first distillation column, components, A, B, and alcohol, and a very small proportion of product amide (C) are drawn off and recycled into the reaction apparatus; and
   drawing a bottom stream comprising the product amide (C) the catalyst, the polymerization inhibitor, and high-boiling by-product from a bottom of the evaporator or first distillation column, and
   feeding the bottom stream to a purifying distillation to obtain the N-alkyl(meth)acrylamide of formula (C)

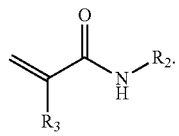
(C)

2. The process of claim 1, wherein
the purifying distillation comprises a two-stage ultrapurifying distillation which comprises a first distillation with at least one low boilers and a lower boiler draw, and a main distillation which removes at least one high boiler from the bottom stream to obtain pure N-alkyl(meth)acrylamide.

3. The process of claim 1, wherein
the amine (B) is dewatered before charging to the reactor by supplying the amine to the distillation column where water is distilled off and then to the reactor.

4. The process of claim 1, wherein
a molar ratio of alkyl(meth)acrylate (A) to amine (B) fed to the reactor is between 1/1 and 2/1.

5. The process of claim 1, wherein
the catalyst comprises a tetraalkyl titanate.

6. The process of claim 1, wherein
the catalyst is employed in an amount of 0.1-10% by weight, based on (meth)acrylate present.

7. The process of claim 6, wherein
the catalyst amount is 0.2-7% by weight, based on (meth)acrylate present.

8. The process of claim 1, wherein
the catalyst comprises:
dioctyltin oxide and isopropyl titanate in a ratio of 2.5:1 (% by weight/% by weight), and
wherein preactivation of the catalyst comprises treatment at 90 to 120° C. for 2 to 3 hours.

9. The process of claim 8, wherein
the catalyst is employed in an amount of 0.1-10% by weight, based on (meth)acrylate present.

10. The process of claim 1, wherein
the polymerization inhibitor comprises a compound selected from the group consisting of phenothiazine, tert-butylcatechol, hydroquinone monomethyl ether, and hydroquinone, and
wherein an amount of the inhibitor is between 10 and 5000 ppm, based on the reaction mixture.

11. The process of claim 1, wherein
the polymerization inhibitor further comprises oxygen.

12. The process of claim 1, wherein
the amine of formula (B) comprises dimethylaminopropylamine.

13. The process of claim 1, wherein
a pressure in the first distillation column is between 2 and 500 mbar.

14. The process of claim 1, wherein
a residence time of the reaction mixture in the reaction apparatus is between 0.5 and 3 hours.

15. The process of claim 1, wherein the reaction mixture is fed to an evaporator and the evaporator is a film evaporator.

16. A N-alkyl(meth)acrylamide obtained by the process of claim 1, wherein a crosslinker content of the N-alkyl(meth)acrylamide is less than 600 ppm.

17. The process of claim 4, wherein the molar ratio of alkyl(meth)acrylate to amine is between 1.05/1 and 1.15/1.

18. The process of claim 2, wherein the amine (B) is dewatered before charging to the reactor by supplying the amine to the distillation column where water is distilled off and then to the reactor.

19. The process of claim 2, wherein a molar ratio of alkyl (meth)acrylate (A) to amine (B) fed to the reactor is between 1/1 and 2/1.

20. The process of claim 19, wherein the molar ratio of alkyl(meth)acrylate to amine is between 1.05/1 and 1.15/1.

* * * * *